Figure 1A:
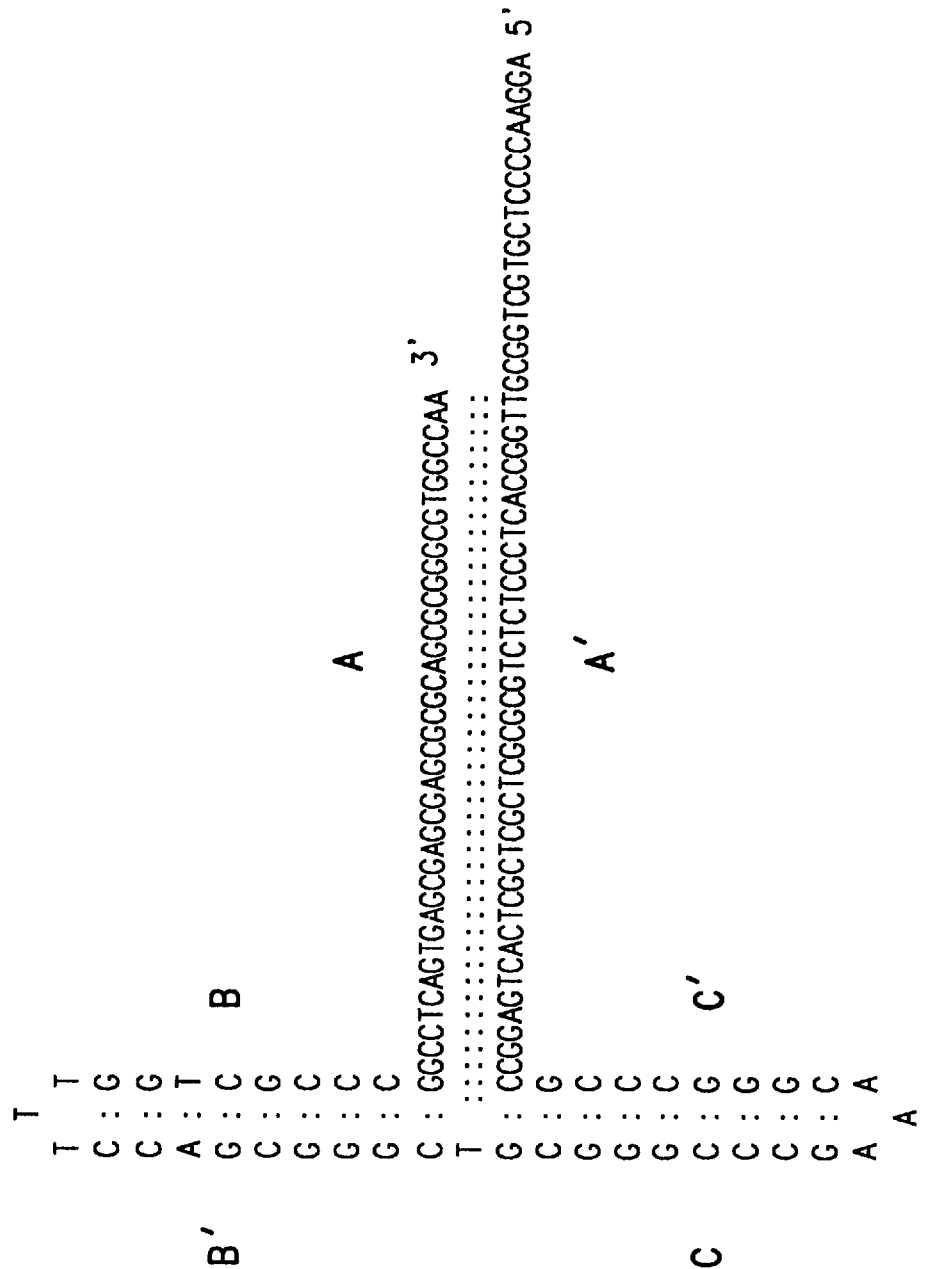

United States Patent [19]
Samulski et al.

[11] Patent Number: 5,869,305
[45] Date of Patent: *Feb. 9, 1999

[54] RECOMBINANT VIRAL VECTOR SYSTEM

[75] Inventors: Richard Jude Samulski; Xiao Xiao, both of Chapel Hill, N.C.

[73] Assignee: The University of Pittsburgh, Pittsburgh, Pa.

[ * ] Notice: The term of this patent shall not extend beyond the expiration date of Pat. No. 5,478,745.

[21] Appl. No.: 440,738

[22] Filed: May 15, 1995

Related U.S. Application Data

[63] Continuation-in-part of Ser. No. 989,841, Dec. 4, 1992, Pat. No. 5,478,745.

[51] Int. Cl.$^6$ ............................ C12N 15/03; C12N 15/86; C12N 5/22; C07H 21/04
[52] U.S. Cl. ................................. 435/172.3; 435/320.1; 435/369; 536/24.1
[58] Field of Search .............................. 435/69.1, 172.3, 435/235.1, 240.2, 320.1, 369; 514/44; 935/32, 34, 70, 71; 536/24.1

[56] References Cited

U.S. PATENT DOCUMENTS

| | | | |
|---|---|---|---|
| 4,797,368 | 1/1989 | Carter et al. | 435/320.1 |
| 5,139,941 | 8/1992 | Muzyczka et al. | 435/172.3 |
| 5,478,745 | 12/1995 | Samulski et al. | 435/320.1 |

OTHER PUBLICATIONS

Samulski et al. (Sep. 1989) J. Virol. 63:3822–3828.

Cheung, A. et al., 1980, "Integration of the Adeno–Associated Virus Genome into Cellular DNA in Latently Infected Human Detroit 6 Cells", J. Virol. 33:739–748.

Berns, K. et al., 1982, "Adeno–Associated Virus Latent Infection", In: Mahey et al, (eds.), Virus Persistence, Cambridge University Press, Cambridge, U.K., pp. 249–265.

Samulski, R.J. et al., 1982, "Cloning of Adeno–Associated Virus into pBR322: Rescue of Intact Virus From the Recombinant Plasmid in Human Cells", Proc. Natl. Acad. Sci. USA 79:2077–2081.

Miller, A.D., 1990, "Retrovirus Packaging Cells", Human Gene Therapy 1:5–14.

Kotin, R. et al., 1990, "Site–Specific Integration by Adeno–Associated Virus", Proc. Natl. Acad. Sci. USA 87:2211–2215.

Samulski, R. et al., 1991, "Targeted Integration of Adeno–Associated Virus (AAV) into Human Chromosome 19", EMBO J. 10:3941–3950.

Muzyczka, N., 1992, "Use of Adeno–Associated Virus as a General Transduction Vector for Mammalian Cells", Current Topics in Microbiol. & Immunol., 158:97–129.

Philip, R. et al., 1994, "Efficient and Sustained Gene Expression in Primary T Lymphocytes and Primary and Cultured Tumor Cells Mediated by Adeno–Associated Virus Plasmid DNA Complexed to Cationic Liposomes", Mol. Cell. Biol. 14:2411–2418.

*Primary Examiner*—George C. Elliott
*Assistant Examiner*—Robert Schwartzman
*Attorney, Agent, or Firm*—Pennie & Edmonds LLP

[57] ABSTRACT

The present invention relates to a system for replication and encapsidation of recombinant DNA fragments into virus particles comprised of adenovirus associated viral (AAV) capsid proteins. The invention provides a means of obtaining recombinant viral stocks that may be used to treat patients suffering from genetic diseases.

25 Claims, 13 Drawing Sheets

5'- AGGAACCCCT AGTGATGGAG TTGGCCACTC CCTCTCTGCG CGCTCGCTCG CTCACTGAGG   60
CCGGGGACC AAAGGTCGCC CGACGCCCGG GCTTTGCCCG GGCGGCCTCA GTGAGCGAGC  120
GAGCGCGCAG AGAGGGAGTG GCCAACTCCA TCACTAGGGG TTCCT - 3'              165

FIG.9

5'- CCCTGTATCC TAAATCAAAT ATCGGACAAG CAGTGTCTGT TATAACAAAA AATCGATTTA   60
ATAGACACAC CAACAGCATG GTTTTATGT GTGCGATAAT TTATAATATT TCGGACAGGG - 3'  120

FIG.10

RECOMBINANT VIRAL VECTOR SYSTEM

This application is a continuation-in-part application of Ser. No. 07/989,841, filed on Dec. 4, 1992, U.S. Pat. No. 5,478,745. This invention was made with government support under grant #5R29 AI25530-03 awarded by the National Institutes of Health. The government has certain rights in this invention.

TABLE OF CONTENTS

1. Introduction
2. Background Of The Invention
3. Summary Of The Invention
4. Brief Description Of The Drawings
5. Detailed Description Of The Invention
   5.1. The AAV Viral Sequences
   5.2. Construction Of Recombinant Vectors Comprised Of AAV Viral Sequences And Heterologous Linked Sequences
   5.3. Production Of Recombinant Virus Stocks
   5.4. Uses Of Recombinant Vectors
6. Example: A Novel 165 Base Pair Terminal Repeat Is The Only cis-Element Required For Adeno-Associated Virus Life Cycle
   6.1. Materials And Methods
      6.1.1. DNA Transfection
      6.1.2. Southern Hybridization
      6.1.3. PCR And Construction Of ITR Plasmid
      6.1.4. Cloning Of Neo-Resistant Cell Lines
   6.2. Results
      6.2.1. Construction Of ITR With Double D Sequence
      6.2.2. PDD-2 Replication Is Dependent On Rep
      6.2.3. Replication And Rescue Is Via AAV Mechanism
      6.2.4. One Double-D In-Cis Is Sufficient For AAV Viability
      6.2.5. Transfection of Double-D Recombinant Vectors

1. INTRODUCTION

The present invention relates to novel recombinant expression vectors that can be used to introduce and/or express a heterologous gene of interest into targeted host cells. The recombinant expression vectors of the invention contain all the necessary information required in cis for site specific integration and/or for replication and encapsidation of the recombinant DNA fragments into virus particles comprised of adenovirus associated viral (AAV) capsid proteins. The novel recombinant expression vectors of the invention provide a means of transferring genetic information, or alternatively, for obtaining recombinant viral stocks that may be used to treat patients suffering from genetic diseases.

2. BACKGROUND OF THE INVENTION

At the present time, treatments for most genetic diseases do little to alleviate the symptoms associated with the genetic disease and considerable effort is currently underway to develop new, safe and effective methods of treatment. Recent progress in the areas of molecular biology and genetic engineering have lead to the isolation and characterization of genes associated with genetic diseases. This in turn has lead to the development of the concept of gene therapy i.e., the replacement or supplement of defective genetic information with normal functional genes, and its potential use for treatment of genetic disorders.

The most well studied models for gene therapy involve gene transfer using recombinant pathogenic viruses to express new genetic information in order to correct disease phenotypes. Until recently, the most widely researched viral vectors for use in gene therapy were the retroviruses (Miller, A. D., 1990, Human Gene Ther. 1:5–14). One problem associated with retroviral use is the random integration of retroviruses into the host genome which can lead to insertional mutagenesis. In addition, the long terminal repeats (LTR) structures located at the ends of the retroviral genome contain promoter/enhancer activity that may lead to activation of genetic loci located adjacent to the integrated viral DNA. For example, integration of retroviral DNA adjacent to a proto-oncogene may lead to inadvertent activation of proto-oncogene expression which may, in turn, lead to transformation and tumorigenesis. This is illustrated, for example, by recent evidence indicating that retrovirus vectors in non-human primates results in T cell lymphomas. More recent efforts in the field of gene therapy have focussed on the development of viral vectors lacking the deleterious characteristics of the retroviruses.

In addition to the retroviruses, the adeno associated viruses have also been studied as an alternative system for delivery of stable genetic information into the cell. The AAV genome is composed of a linear single stranded DNA molecule of 4680 nucleotides which contains major open reading frames coding for the Rep (replication) and cap (capsid) proteins. Flanking the AAV coding regions are the two 145 nucleotide inverted terminal (ITR) repeat sequences that contain palindromic sequences that can fold over to form hairpin structures which function as primers during initiation of DNA replication (FIG. 1). In addition, the ITR sequences are needed in cis, for viral integration, rescue from the host genome and encapsidation of viral genomic DNA, into mature virions (Muzyczka, N. 1992, Current Topics in Microbiology & Immunology. 158, 97–129).

AAV can assume one of two pathways upon infection into the host cell. In the presence of helper virus, AAV will enter the lytic cycle whereby the viral genome is transcribed, replicated, and encapsidated into newly formed viral particles. In the absence of helper virus function, the AAV genome integrates as a provirus into of the host cell genome through recombination between the AAV termini and host cell sequences (Cheung, A. et al., 1980, J. Virol. 33:739–748; Berns, K. I. et al., 1982, in Virus Persistence, eds. Mahey, B. W. J., et al. (Cambridge Univ. Press, Cambridge), pp. 249–265).

Characterization of the proviral integration site and analysis of flanking cellular sequences indicates that AAV viral DNA integrates specifically into the long arm of human chromosome 19 (Kotin, R. M. et al., 1990, Proc. Natl. Acad. Sci. USA 87:2211–2215; Samulski, R. J. et al., 1991, EMBO J. 10:3941–3950). This particular feature of AAV reduces the likelihood of insertional mutagenesis resulting from random integration of viral vector DNA into the coding region of a host gene. Furthermore, in contrast to the retroviral LTR sequences, the AAV ITR (inverted terminal repeat) sequences appear to be devoid of transcriptional regulatory elements, reducing the risk of insertional activation of proto oncogenes.

Recent work with AAV has been facilitated by the discovery that AAV sequences cloned into prokaryotic vectors are infectious (Samulski, et al. 1982, Proc. Natl. Acad. Sci. U.S.A. 79:2077–2081). For example, when a plasmid containing an intact AAV genome is transfected into cells in the presence of helper virus, AAV can be rescued out from the plasmid vector and enter the lytic pathway leading to production of mature virions. In the absence of helper virus the recombinant AAV vector will integrate into the host cell genome and remain as a provirus until the cell subsequently becomes infected with a helper virus.

One problem associated with the use of vectors containing an intact AAV genome is the size limitations imposed on the vectors by the packaging of DNA fragments into mature viral particles. Prior to the present invention it was unknown what viral sequences were required for replication, and encapsidation of the DNA into viral particles, or alternatively, for integration of vector DNA into the host genome. The present invention defines a novel 165 bp sequences derived from AAV that can function to direct the replication and encapsidation of DNA into viral particles and/or the integration of vector DNA into the targeted host genome.

3. SUMMARY OF THE INVENTION

The present invention relates to the in vitro synthesis of a novel 165 basepair fragment of DNA which contains AAV ITR sequences and which can be synthesized in vitro and used to engineer expression vectors and/or vectors useful for genetic therapy. This 165 bp DNA sequence, herein referred to as the "double-D sequence," is in a novel configuration not found to exist in wild type AAV.

The invention is based, in part, on the ability of the double-D sequence to provide sufficient information, in cis, for converting a circular duplex DNA molecule into a linear replicating molecule with covalently closed ends. The replicating DNA molecule may be either encapsidated into mature AAV virions, or integrated into the host genome. A particularly significant feature of the circular duplex DNA molecule is that the process of conversion into a linear molecule, and the replication and integration into the host genome is completely effected through the double-D sequences, thus ensuring that the heterologous gene sequences of interest remain intact.

The discovery that the majority of the AAV genome is not needed, in cis, for replication, packaging and/or integration allows one to insert larger fragments of DNA into the recombinant vectors. In addition, the discovery that the 165 double-D sequence is sufficient for targeting vector DNA to chromosome 19 allows the insertion of any sized DNA fragment into the recombinant vectors, thereby removing any size restraints.

Nucleotide sequences which may be used in accordance with the invention include derivatives and analogs of the double-D sequences disclosed herein that are functionally equivalent in that they retain their ability to provide information, in cis, for replication encapsidation, integration and rescue of recombinant DNA. In particular, double-D derivatives may contain additions, substitutions or deletions of the double-D nucleotide sequences while retaining their biological function.

The invention provides an in vivo system for replication and packaging of recombinant DNA into mature virions. Viral stocks containing the recombinant DNA encapsidated into mature virions, may be obtained by transfection of expression vectors into a host cell expressing helper function. The resulting recombinant viral stocks afford a convenient and efficient means for transfer of genetic information into any cell or tissue of choice.

Alternatively, the double-D constructs may be delivered into host cells using a variety of DNA transfer methods such as electroporation, DEAE-dextran, DNA gun, liposomes etc. One particular advantage associated with these delivery methods is the absence of size restraints on the size of the recombinant vectors.

The transfer of genetic information into host cells, using either viral stocks or transfection of recombinant constructs, may have applications in gene therapy wherein the desired goal is correction of a given genetic abnormality through expression of the normal complement of the defective gene.

The invention also relates to in vitro treatment of recombinant viral vectors and/or vectors useful for genetic therapy with bacterial gamma delta resolvase prior to transfection. Genetic engineering of resolvase recognition sequences into recombinant vectors creates the option of removing bacterial plasmid sequences which would normally be included as part of the linear, replicated, and encapsidated DNA molecule. Removal of these bacterial sequences, prior to replication and encapsidation, allows the maximum amount of space for insertion of foreign DNA sequences of interest into the expression vectors.

The invention is described by way of examples in which an AAV double-D fragment is amplified in a polymerase chain reaction (PCR) and inserted into a plasmid vector. Transfection and site specific integration of these double-D recombinant vectors into the host genome indicates that double-D sequences, in the presence of viral REP protein, are sufficient to direct site specific integration of vector DNA. In addition, plasmid vectors containing the double-D sequences were capable of being replicated and assembled into viral particles. Thus, the present invention provides a method for encapsidating recombinant DNA into viral particles that may be used for gene therapy.

4. BRIEF DESCRIPTION OF THE DRAWINGS

Figure 1B:
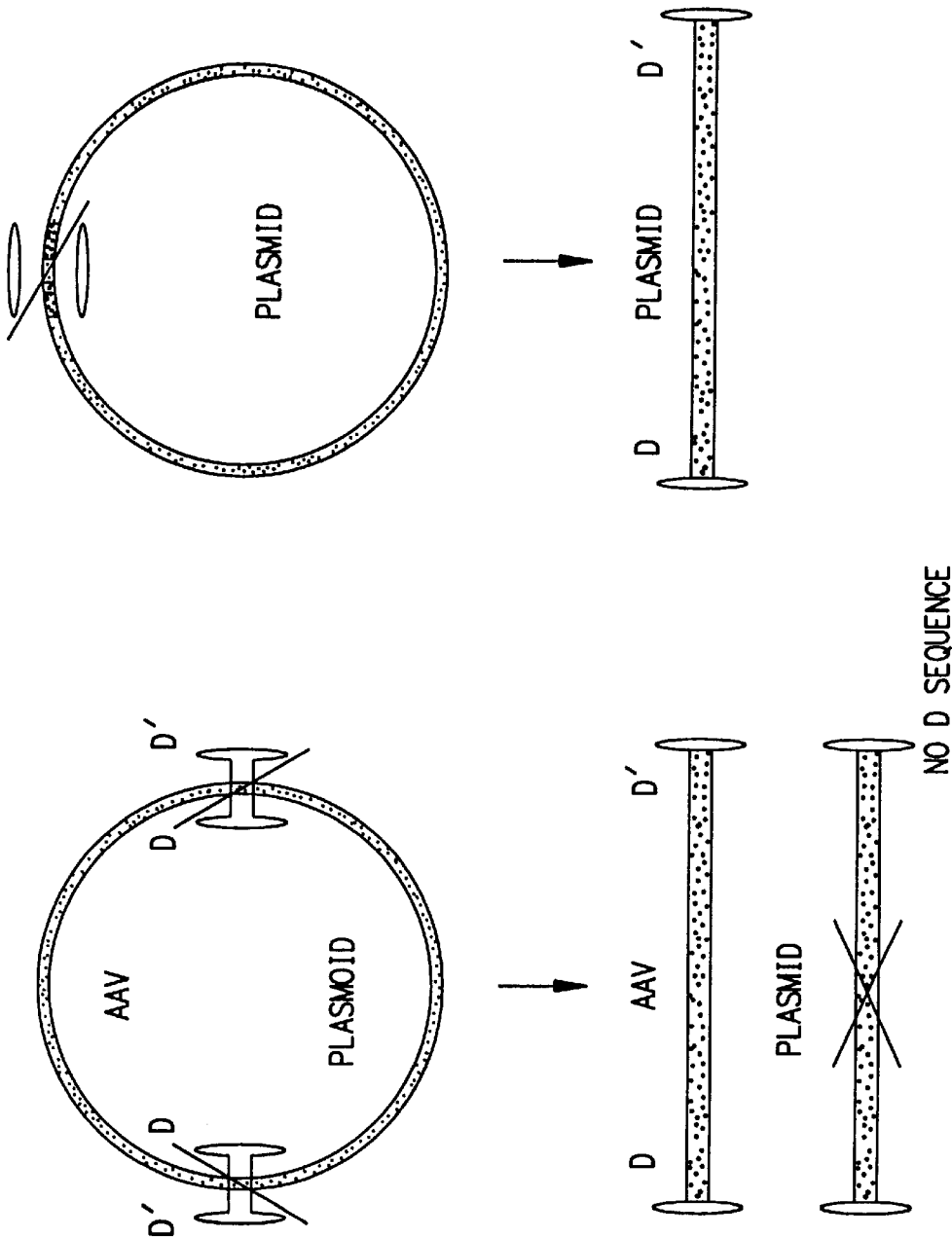
Figure 1C:
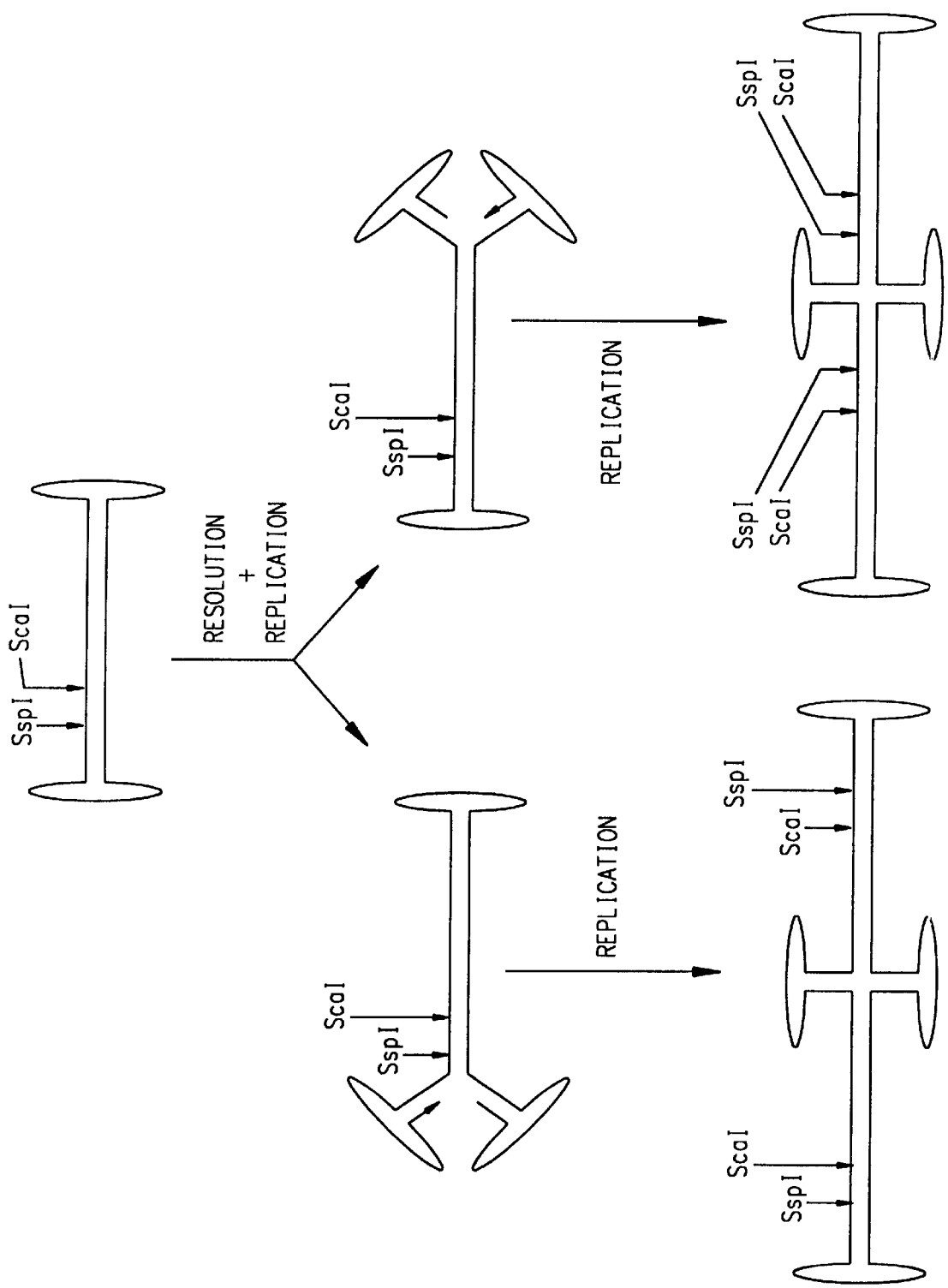

FIGS. 1A, 1B and 1C AAV rescue and replication mechanisms. FIG. 1A Inverted terminal repeats (ITR) may fold back through the base-pairing of A,A', B,B',C,C' sequences to form a T-shape structure (SEQ ID NO: 6). FIG. 1B Excision of infectious plasmid at the ITR sites yields two linear DNA fragments: AAV and the plasmid vector. FIG. 1C Predicted fragments generated from double D plasmid after rescue from plasmid circular form to linear with covalent closed ends.

Figure 2:
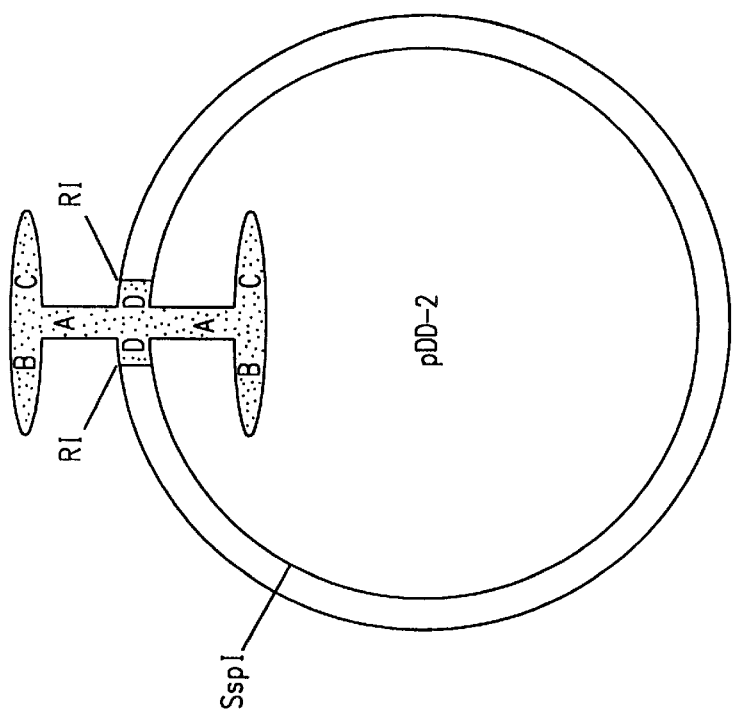
Figure 2:
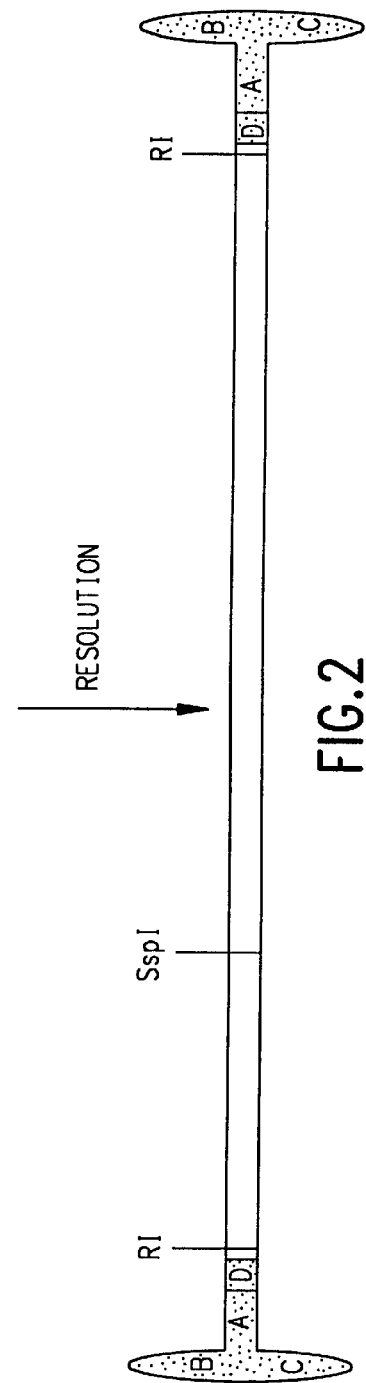

FIG. 2. Rescue Intermediate from circular double-D plasmid.

Figure 3A:
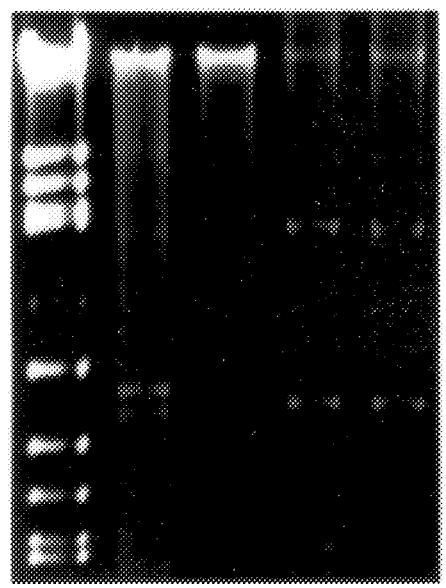
Figure 3B:
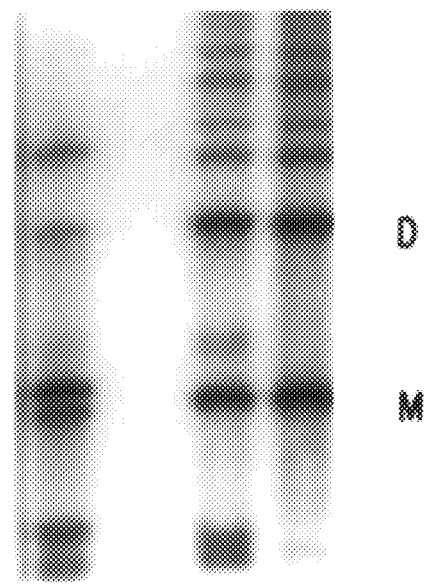

FIGS. 3A and 3B Replication assay for the plasmid containing the double-D inverted terminal repeat. Plasmid pDD-2 was transfected into Ad5 infected 293 cells with or without cotransfection of the helper plasmid pAAV/Ad. Low molecular weight DNA was extracted 48 hrs. post infection and separated on a 1% agarose gel with or without DpnI digestion. FIG. 3A Ethidium bromide staining of the gel. FIG. 3B Southern blot with $^{32}$P labeled plasmid pGEM 3 z probe.

Figure 4A:
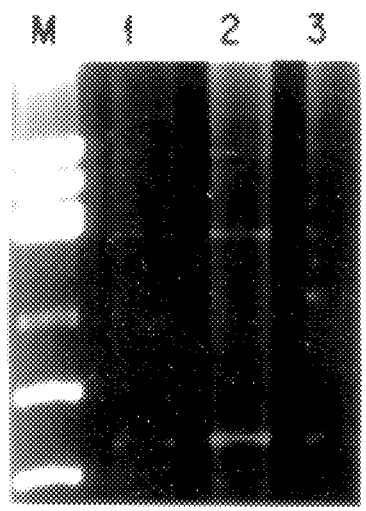
Figure 4B:
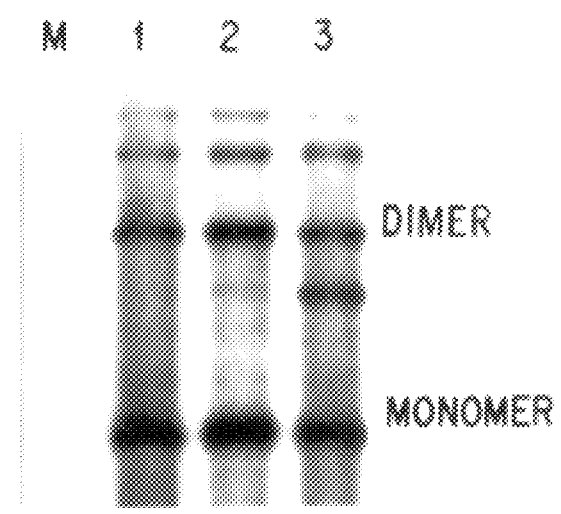

FIGS. 4A and 4B Comparison of replication of pDD-2 with psub201 and pSM620. Plasmid pDD-2 was cotransfected with equal amounts of either pAAV/Ad (lane 1), psub201 (lane 2) or pSM620 (lane 3) into Ad5 infected 293 cells. Low molecular weight DNA was extracted and digested with DpnI and analyzed on a 1% agarose gel. FIG. 4A Ethidium bromide staining. FIG. 4B Southern blot with an ITR oligonucleotide probe.

Figures 5A, 5B:
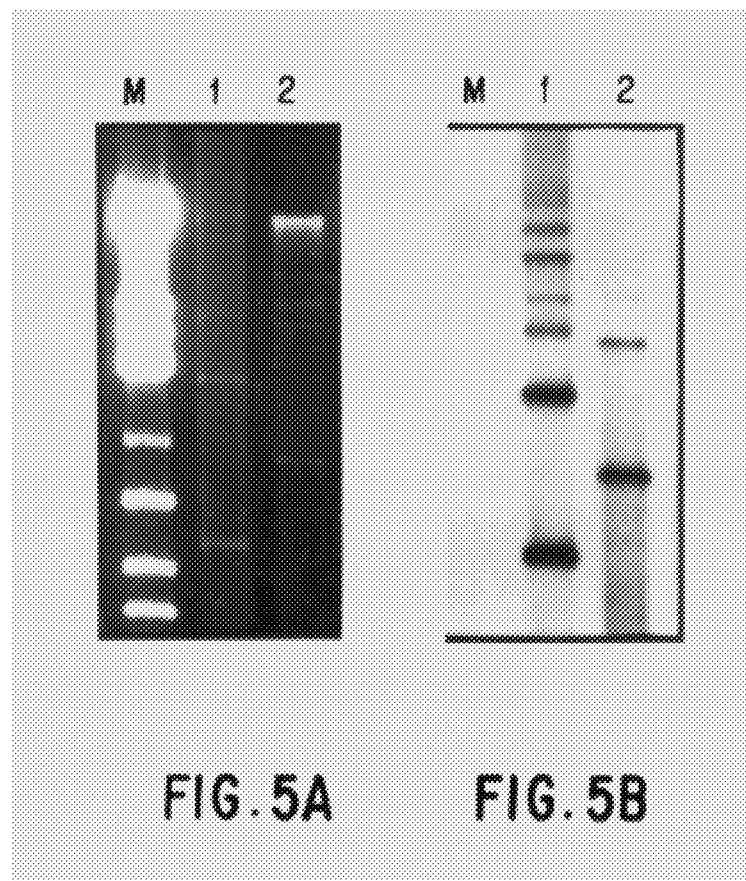

FIGS. 5A and 5B. Replication assay for double-D plasmids with different sizes. pDD-2 or pDD-neo were cotransfected with helper pAAV/Ad into Ad5 infected 293 cells. Low molecular weight DNA was extracted and digested with DpnI and analyzed on a 1% agarose gel.

FIG. 5A Ethidium bromide staining. FIG. 5B Southern blot with $^{32}$P labeled plasmid pGEM 3Z probe.

Figure 6:
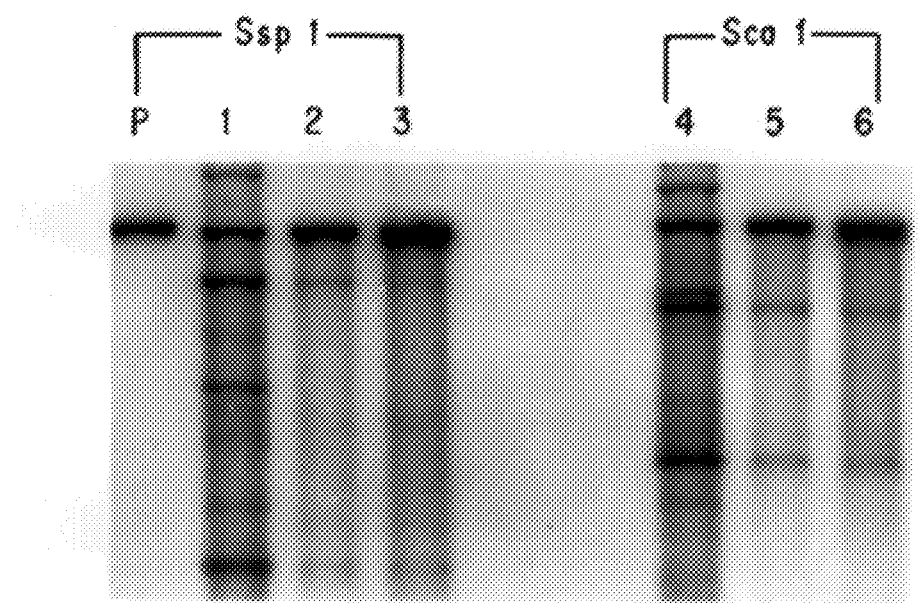

FIG. 6. Restriction analysis of rescue and replication of pDD-2. Plasmid pDD-2 was transfected into Ad5 infected or uninfected 293 cells with or without the cotransfection of helper plasmid pAAV/Ad. Low-molecular-weight DNA was digested with either SspI or ScaI and separated on a 1% agarose gel. Southern blot was done with a $^{32}$P labeled ITR probe.

Figure 7:
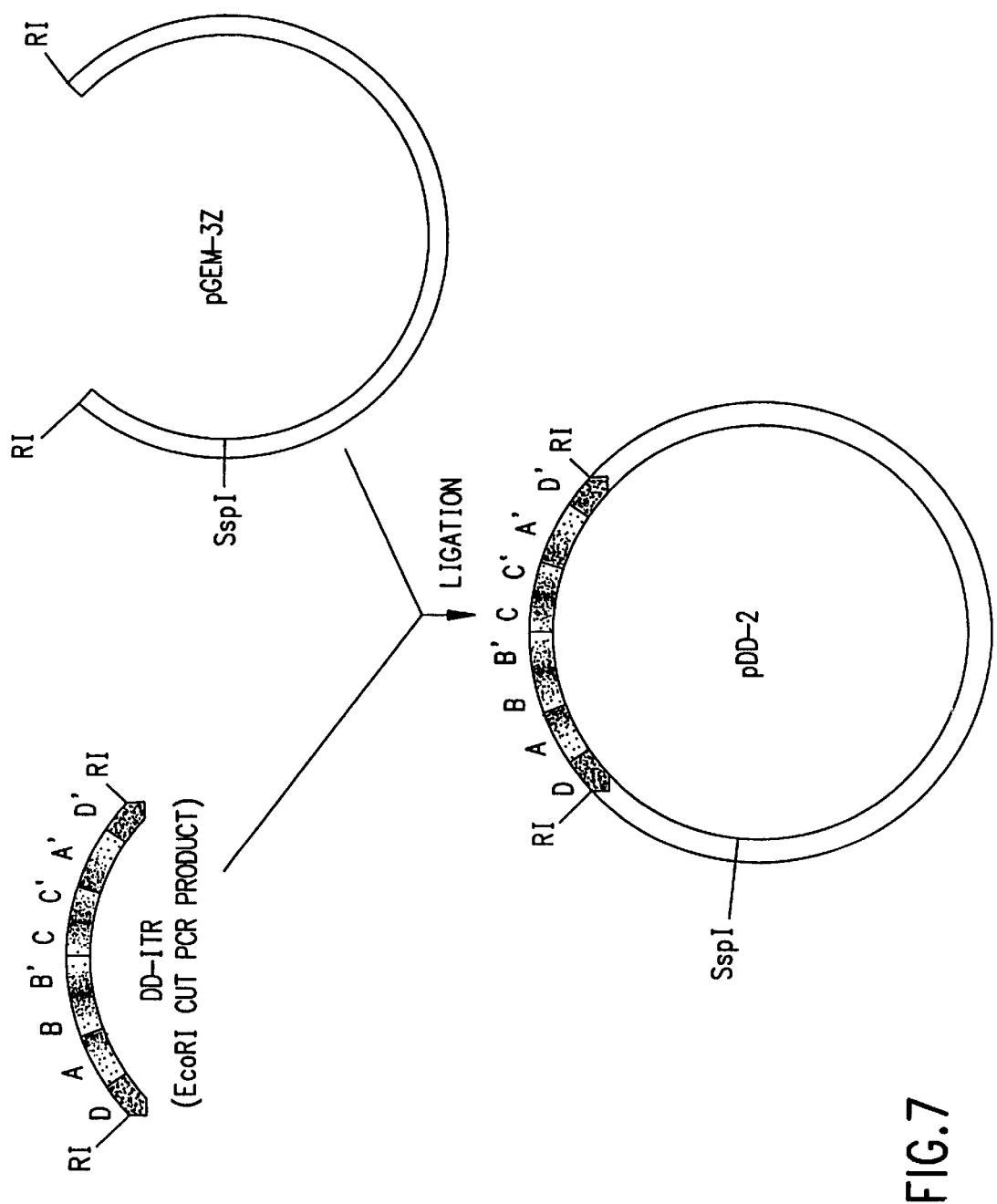

FIG. 7. Cloning of PCR-amplified and EcoRI cut double-D into EcoRI site of plasmid pGEM-3'Z.

Figure 8:
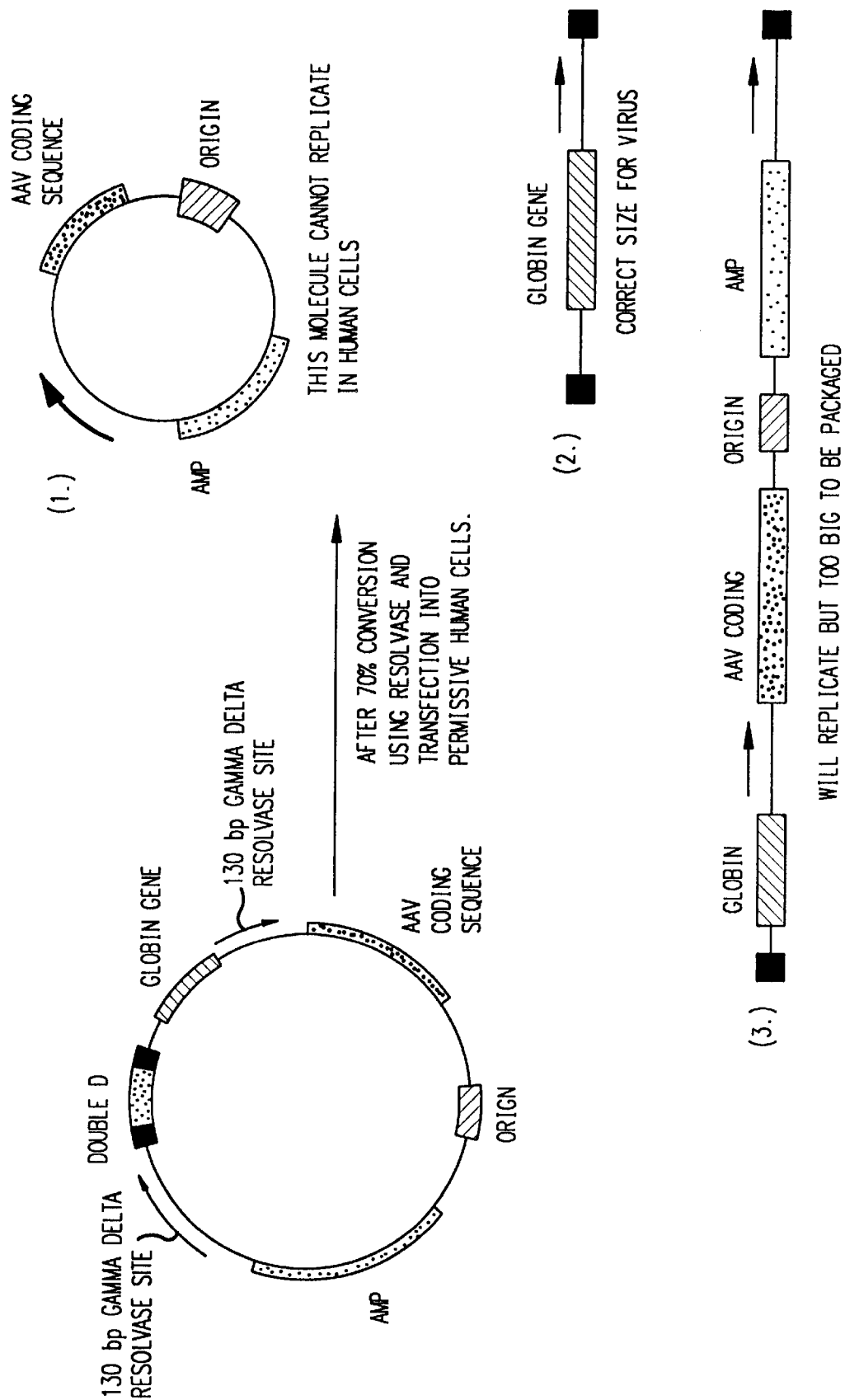

FIG. 8. In-vitro replication of parental plasmid containing resolvase sequences.

FIG. 9. Double-D sequence (SEQ ID NO: 1).

FIG. 10. Bacterial Gamma Delta Resolvase recognition sequence (SEQ ID NO: 2).

Figure 11:
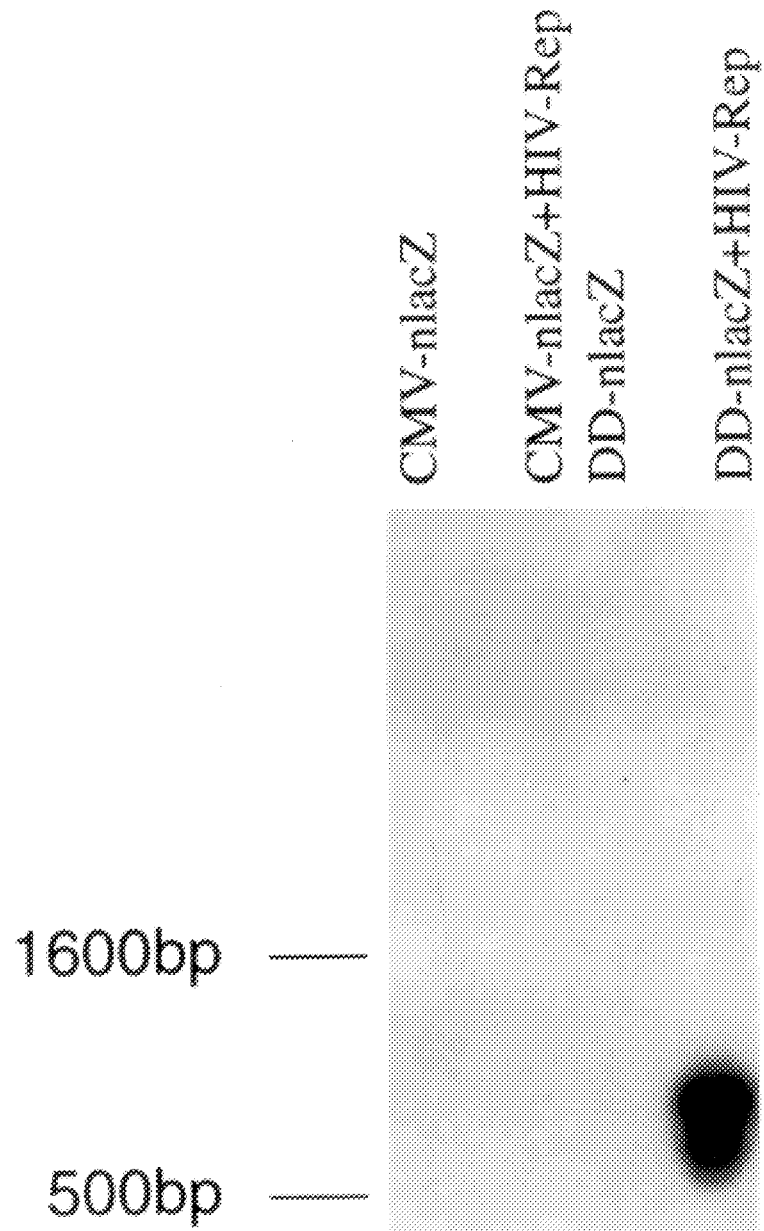

FIG. 11. PCR amplification of DD-cellular junctions. Genomic DNA was isolated from pooled FACS-sorted 293 cells that has been transfected by different combination of CMV-nLacZ, DD-nLacZ and HIV-Rep plasmid. The first round PCR was performed with JUS3A and RI-Left, the second round PCR reaction was carried out with CR2 and RI-left primers. The Southern blot was probed with a $^{32}$P labelled BamHI fragment corresponding to a region chromosome 19.

Figure 12:
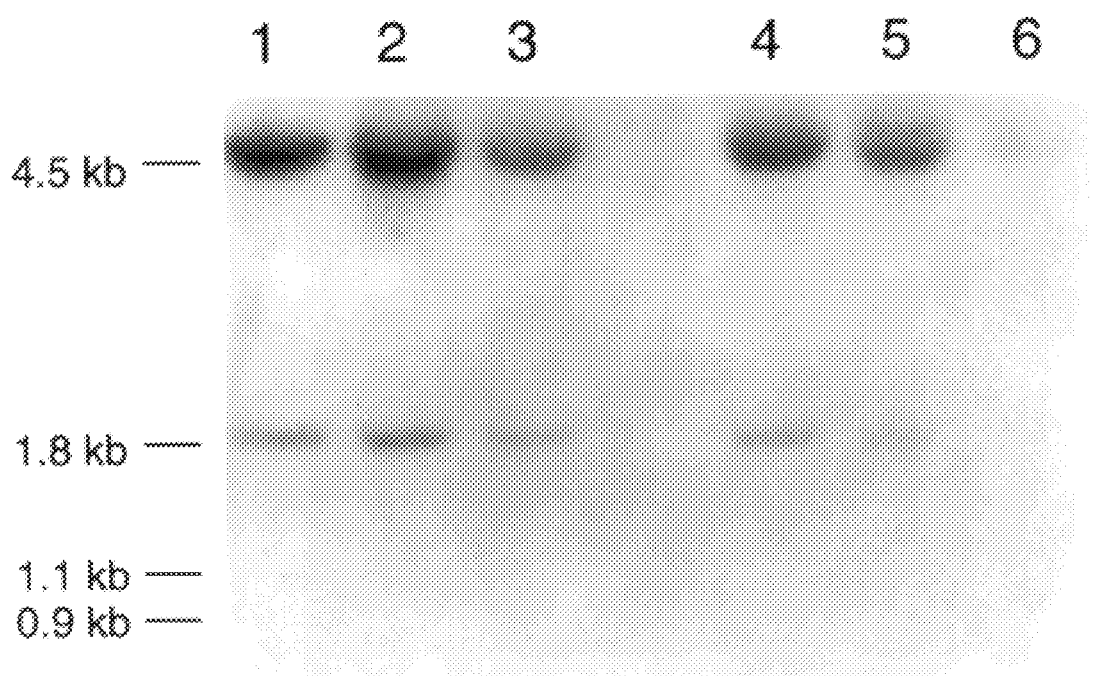

FIG. 12 Southern blot analysis of the integrated plasmids in FACS sorted 293 genomic DNA. Each lane contains 10 μg of DNA digested by ScaI, PstI and KpnI. The DNA was fractionated on 7% gel and the probe was made from DD-nLacZ plasmid. Lane 1 to 6, 293 cells transfected by DD-nLacZ plasmid, DD-nLacZ plasmid+Rep, DD-nLacZ plasmid+HIV-Rep, CMV-nLacZ plasmid, CMV-nLacZ plasmid+REP, CMV-nLacZ plasmid+HIV-Rep.

5. DETAILED DESCRIPTION OF THE INVENTION

The present invention relates to in vitro construction of a novel modified AAV ITR nucleotide sequences, herein referred to as the double-D sequence. The invention is based, in part, on the synthesis of a double-D DNA fragment using PCR technology, and the demonstration that this fragment provides sufficient information in cis for replication and encapsidation of recombinant DNA fragments into mature AAV virions, or the specific integration of recombinant DNA into the host genome. The recombinant DNA fragments need not encode any viral proteins thereby providing a safe method for the transfer of genetic information into the host genome.

The invention is based on the discovery that the cis-acting double-D sequences, in conjunction with trans-acting AAV REP protein, are sufficient for site specific integration of recombinant DNA fragments into chromosome 19 of the host genome. The invention relates to the use of the double-D DNA sequences in recombinant vectors and the use of these vectors for gene replacement therapies.

The double-D sequences may be genetically engineered into vectors designed to introduce and/or express a heterologous gene of interest. For use in gene therapy, the heterologous gene of interest may represent the normal or wild-type version of a defective or mutant gene associated with a given genetic disease. The recombinant vectors, in addition to containing the coding region for the gene of interest and the double-D sequences, may contain other necessary regulatory elements such as promoter/enhancer elements to drive expression of the gene product in the host, and translation and polyadenylation signals. The selection of promoter and enhancer regions will rely on the desired level and tissue specific expression of the gene of interest.

The genetically engineered vectors containing the double-D sequences can be transfected into host cells utilizing any of the techniques frequently employed by those skilled in the art for introducing DNA into mammalian cells. For example, methods including but not limited to electroporation, DEAE-dextran mediated DNA transfer, DNA guns, liposomes, direct injection, etc. may be utilized to transfer recombinant vectors into host cells. Alternatively, the DNA may be transferred into cells through conjugation to proteins that are normally targeted to the inside of a cell. For example, the DNA may be conjugated to viral proteins that normally target viral particles into the targeted host cell.

Host cells may be transfected in vivo or in vitro. For example, cells such as bone marrow cells, may be removed from the host, transfected with the recombinant double-D vectors and returned to the host. Alternatively, recombinant double-D vectors may be encapsulated into liposomes for in vivo transfer of genetic information into host cells.

One significant advantage associated with transfection of double-D vectors into host cells is the absence of restraints on the size of the recombinant vectors. This is in contrast to the size limitations imposed by the packaging of DNA fragments into mature virus particles. Another advantage is that there is no risk of generating infectious viral particles when the treated individual later becomes infected with helper virus and AAV.

The recombinant vectors may also be transfected into a host cell line that provides helper virus function and supplies in trans the REP and CAP proteins allowing one to obtain a recombinant virus stock (Muzyczka, N. 1992, Current Topics in Microbiology and Immunology 158:97–129). The resulting virus stock may then be used as a highly efficient means of delivery and transfer of new genetic information into targeted cells or tissues of choice.

5.1. THE DOUBLE-D SEQUENCES

The AAV genome consists of 4680 nucleotides containing two open reading frames that encode the REP (replication) and CAP (capsid) proteins. Located at both ends of the genome are 145 bp inverted terminal repeats (ITRs), which are unique in that' they not only basepair with each other, but also individually fold back on themselves through the basepairing of A, A', B, B', C, C' sequences to form a T-shaped structure for DNA replication when single stranded (FIG. 1A).

When a plasmid containing an intact AAV genome is transfected into helpervirus infected cells, AAV can be rescued or replicated out from the plasmid vector and enter the viral lytic cycle leading to production of mature virions. If the AAV coding region is deleted and replaced by heterologous DNA sequences, the recombinant AAV can still complete the viral lytic cycle provided the ITRs are intact and the REP and CAP proteins, or functional equivalents, are supplied in trans. However, if one of the two ITR sequences are deleted no viral DNA replication is observed indicating that both ITRs are required for AAV viability.

The invention is based, in part, on the discovery that the following 20 basepair D sequence (AGGAACCCCTAGTGATGGAG) (SEQ ID NO: 5), present in the ITR sequence I required for viral replication. This is initially demonstrated by the inability of viral mutants with deleted D sequences to replicate their DNA Furthermore, during the replication of a terminal resolution site mutant, natural deletions were found to occur only towards the A sequence of the ITR and not towards the D end, suggesting a selection process for retention of D sequences.

In order to elucidate further the function of the D sequences, a novel modified terminal repeat structure was constructed containing a single 145 bp ITR sequence with an additional 20 bp D' sequence (FIG. 9) (SEQ ID NO: 1) (See Section 6.13, infra). The resulting 165 bp sequence has not been identified in any naturally occurring virus. Using AAV DNA as template and a single primer derived from the D sequence of the AAV ITR sequence plus a 6 bp EcoRI recognition site on the 5' end, a polymerase chain reaction was performed that resulted in a DNA fragment comprised of an ITR flanked on either side by D or D' sequences as well as EcoRI sites. The PCR generated DNA fragment was cleaved by EcoRI and subsequently cloned into the EcoRI site of pGEM3Z (FIG. 7).

To determine whether the double-D was able to function in replication, encapsidation, integration and rescue of recombinant DNA, a recombinant plasmid containing the double-D structure was transfected into cells. Results from these experiments indicate that the novel double-D sequence is sufficient to carry out the functions normally required of two wild type ITRs during a lytic AAV viral infection.

In addition, cotransfection of recombinant DNA containing double-D sequences and DNA encoding AAV REP protein indicate that the double-D sequences and the REP protein are all that is required for site specific integration into the host genome. (See Section 6.2.3. and Section 6.2.4., infra). Analysis of the viral integration site indicates that integration takes place through the ITR sequences, thus ensuring that the vector sequences, i.e. those sequences containing heterologous sequences of interest remain intact.

In addition to the double-D sequence of FIG. 9 (SEQ. ID NO.: 1), nucleotide sequences capable of hybridizing to the double-D sequences (SEQ ID NO: 1) under highly or less highly stringent hybridization conditions are well within the scope of the invention. Highly stringent hybridization conditions may be defined as hybridization to filter-bound DNA in 0.5M NaHPO4, 7% sodium dodecyl sulfate (SDS), 1 mM EDTA at 65° C., followed by washing in 0.1×SSC/0.1% SDS at 68° C. (Ausubel F. M. et al., eds, 1989, Current Protocols in Molecular Biology, Vol. I, Green Publishing Associates, Inc., and John Wiley & Sons, Inc., New York at p. 2.10.3). Less highly stringent conditions, such as moderately stringent conditions, may be defined as hybridizations carried out as described above, followed by washing in 0.2×SSC/0.1% SDS at 42° C. (Ausubel et al., 1989, supra).

In an additional embodiment of the invention, double-D sequences from other adenovirus-associated viral subtypes which form hairpin structures, may be used for isolating double-D DNA fragments. Alternatively, altered nucleotide sequences which may be used in accordance with the invention include derivatives and analogs of the double-D sequence that are functionally equivalent in that they retain their ability to provide information, in cis, for replication, encapsidation, integration and rescue of recombinant DNA. In particular, double-D derivatives may contain additions, substitutions or deletions of nucleotide sequences but still retain biological function.

The present invention includes methods for identifying additions, substitutions or deletions of double-D sequences that retain double-D function. Alterations in the double-D sequences may be generated using a variety of chemical and enzymatic methods which are well known to those skilled in the art. For example, oligonucleotide-directed mutagenesis may be employed to alter the double-D DNA sequence in a defined way and/or to introduce restriction sites in specific regions within the double-D sequence. Alternatively, deletion mutants may be generated using DNA nucleases such as Bal 31 or Exo III and S1 nuclease. Progressively larger deletions in the double-D sequences may be generated by incubating said DNA with nucleases for increased periods of time. (See Ausubel, et al., 1989 Current Protocols for Molecular Biology, for a review of mutagenesis techniques).

The altered double-D sequences may be evaluated for their ability to provide information, in cis, for replication, encapsidation, integration and rescue of recombinant DNA using, for example, any of the methods described herein (See e.g., Section 6 supra). It is well within the scope of the present invention that any altered double-D sequences that retain their ability to provide information, in cis, for replication, encapsidation, integration and rescue of recombinant DNA may be incorporated into recombinant expression vectors which may then be employed for transfer of genetic information into host cells.

A number of advantages are associated with the use of recombinant vectors containing double-D sequences. One advantage is that the double-D sequences enable these vectors to convert from circular duplex molecules into linear replicating molecules with covalently closed hairpin ends (see FIG. 6). This is believed to be essential as the formation of linear molecules is a major prerequisite for successful integration of recombinant DNA into the host genome. The spontaneous formation of linear molecules, in the absence of any viral proteins, represents a significant advantage over the use of other AAV based vectors which require linearization prior to introduction by transfection into host cells.

Additionally, the formation of linear replicating molecules and the integration of the replicated molecules via the double-D sequences ensures that the DNA sequences ensures that the DNA requires encoding the gene of interest remain intact.

5.2. CONSTRUCTION OF RECOMBINANT VECTORS COMPRISED OF DOUBLE-D SEQUENCES AND HETEROLOGOUS LINKED SEQUENCES

The double-D sequences (SEQ ID NO: 1) of the invention provide all the necessary information for directing the replication and encapsidation of recombinant DNA into mature virions. A DNA fragment containing a double-D nucleotide sequence may be obtained by any number of methods commonly used in the art. In a specific embodiment, described herein, a polymerase chain reaction (PCR) was used to obtain a double-D DNA fragment using AAV DNA as template and a primer derived from the D sequence of the AAV ITR. The rationale for this approach is based on the expected secondary structure of the natural ITR sequence.

In the first round of the PCR reaction, the AAV viral ITR forms a hairpin structure and self-primes the elongation process to produce a long T-shaped hairpin structure containing D and D' on the stem. Upon denaturation, this DNA serves as template for a single-primed PCR reaction. Alternative methods for isolating a double-D DNA fragment, include but are not limited to chemically synthesizing the DNA sequence.

Standard recombinant DNA methods may be used for insertion of novel double-D sequences into recombinant vectors which may include, for example, plasmid or cosmid vectors. The methods include in vitro recombinant DNA techniques, synthetic techniques and in vivo recombination/genetic recombination. For example, the double-D DNA sequence may be amplified in a PCR reaction using oligonucleotide primers that add an appropriate restriction endonuclease recognition site onto each end of the amplified DNA fragment (See Section 6.1.3). Alternatively, any restriction site desired may be produced by ligating nucleotide sequences (linkers), comprising specific chemically synthesized oligonucleotides encoding restriction endonuclease recognition sequences, onto the termini of the amplified double-D fragment into an expression vector having complementary cohesive termini.

A variety of host recombinant vector systems may be utilized equally well by those skilled in the art. The recombinant vectors could contain bacterial plasmid sequences necessary for replication in E.coli or the cis acting double-D sequence could be ligated directly to the gene of interest. In addition, plasmids will contain DNA sequences coding for a heterologous gene of interest, inserted between the appropriate transcriptional/translational control sequences and polyadenylation signals. A variety of promoter/enhancer elements may be used depending on the level and tissue specific expression desired. Promoters produced by recombinant DNA or synthetic techniques may be used to provide for transcription of the inserted gene of interest. Specific initiation signals are also required for efficient translation of inserted protein coding sequences. These sequences include the ATG initiation codon and adjacent sequences. In addition, polyadenlylation signals may be included to increase the stability of transcribed mRNA.

One potential drawback of the AAV viral vector system is the size limitation imposed by the inability of DNA fragments larger than 5 Kb to be packaged into mature virus particles. In any given expression vector, 2–3 Kb of DNA sequence derives from bacterial plasmid sequences which are required for propagation of plasmid in *E. coli*. These DNA sequences include origin of replication (ori) sequences and genes that confer resistance to antibiotics such as ampicillin and tetracycline. In effect, this leaves only 2 Kb of space for insertion of heterologous genes of interest.

The following particular, non-limiting embodiment of the invention addresses this size limitation problem. To increase the amount of space available for cloning of sequences of interest, a bacterial recombination system (gamma delta) may be used to resolve plasmids in such a manner that the majority of the bacterial plasmid DNA sequences will be recombined out of any given recombinant plasmid construct in vitro, thereby allowing for the maximum amount of space for insertion of foreign genes. The gamma delta resolvase sequences may be used in a variety of viral vector systems, not limited to AAV systems, as a general method for increasing the space available for insertion of foreign genes.

The parental double-D expression vector plasmid may be engineered to contain, in addition to the double-D sequence, two copies of the gamma delta resolution site (FIG. 10) (SEQ ID NO: 2) (120 basepairs) in the correct orientation so as to promote recombination when resolved in vitro with gamma delta resolvase enzyme. In the presence of gamma delta resolvase, the recombinant plasmid should be converted into two circular DNA molecules (FIG. 8). One plasmid molecule should contain the primary bacterial plasmid sequences along with a copy of the gamma delta resolution site. The other resolved plasmid molecule would be expected to contain the double-D cis acting sequences, one copy of a gamma delta resolution site and the coding region for the gene of interest. It is this plasmid molecule which will be converted, in the presence of helper virus and the viral REP and CAP proteins, into a linear replicating molecule which will then be encapsidated into mature viral particles.

Currently, a second plasmid is required to supply the CAP and REP proteins which are needed to convert circular plasmid molecules into replicating linear DNA fragments. In a further particular embodiment of the invention, plasmids containing the gamma delta resolution sites may be engineered to also contain the coding regions for the required viral REP and CAP functions. Normally the REP and CAP coding sequences would be excluded from the expression vector because they further limit the size of your insert. Using the in vitro recombination system, these coding regions may be included in the plasmid construct, since they will be recombined out during resolution through the two gamma delta resolution sites by the resolvase enzyme (FIG. 8). The products are two concatenated DNA molecules.

Because the in vitro gamma delta reaction is a linear reaction, the amount of resolved molecules may be controlled in the in vitro resolving reaction to generate desired ratios of parental plasmid to resolved circles. The mixture of plasmids can then be transfected into the host cell. This introduces one circular molecule containing the AAV REP and CAP genes required in trans for a productive replication, and the other circular molecule contains the double-D sequences and the gene of interest. The double-D circular molecule may be replicated into a linear DNA molecule which may subsequently be encapsidated into viral particles by the trans factors introduced on the REP/CAP circular plasmid.

The present invention further provides for the analogous use of the above-described gamma delta resolvase system to first propagate plasmids that comprise (i) a recombinant viral vector sequence comprising a gene of interest, (ii) viral genes providing helper functions, and (iii) two gamma delta resolvase recognition sequences flanking the viral vector sequence (SEQ ID NO: 2) and, second, to separate recombinant viral vector sequences comprising the gene of interest from the remaining plasmid sequence using resolvase enzyme. According to these methods, the virus from which the vector and helper functions are derived may be any suitable virus including but not limited to AAV, a retrovirus, adenovirus, or herpes virus. In preferred embodiments the viral vector portion of the plasmid comprises the double-D sequence or, alternatively, both AAV ITR's. In general, the viral vector protein comprises sequences necessary for encapsidation and transcription of the gene of interest.

5.3. PRODUCTION OF RECOMBINANT VIRUS STOCKS

The invention relates to a method for replicating and encapsidating a recombinant DNA molecule into an AAV particle which comprises culturing a eukaryotic cell containing helper virus, recombinant DNA encoding AAV REP and CAP proteins, and a recombinant nucleic acid containing a DNA sequence of interest and the 165 base pair double-D sequence.

To generate recombinant viral stocks, the double-D recombinant expression vector plasmid may be transfected into a host cell line that is capable of providing helper virus function, and supplying in trans AAV REP and CAP proteins. The REP and CAP proteins are required for replication and encapsidation of the linear recombinant DNA into mature viral particles.

The REP and CAP proteins may be supplied in trans by transfection of the host cell line with a recombinant plasmid that is capable of coding for each of the proteins. DNA transfections may be carried out using methods well known to those skilled in the art. These may include DNA transfection by lipofection, electroporation or calcium phosphate precipitation (Ausubel, et al., 1989, in Current Protocols for Molecular Biology, Green Publishing Associates, Inc. and John Wiley & Sons, Inc., New York). The plasmid is transfected into the host cell line with the intention of either transiently or stably expressing the REP and CAP proteins. In a specific embodiment, described in Section 6.1., the plasmid pAAV/AD containing the AAV coding regions, was transfected into a host cell for the purpose of expressing the REP and CAP proteins.

In another embodiment, the double-D expression vector may be engineered to directly express the REP and CAP proteins. In this case, it is also important to include the gamma delta resolvase sequences in the plasmid vector, so that the REP and CAP coding regions may be recombined out during an in vitro resolvase reaction so as not to impose a size limitation on the insert of foreign DNA.

In addition to expressing the viral REP and CAP proteins, the host cell lines must be able to provide helper virus function. Both adenovirus and herpes simplex virus may serve as helper viruses for replication of DNA fragments containing the double-D sequences. Any host cell permissive for infection by either of these two viruses or any virus that acts as a helper virus for AAV, may be used in the practice of the invention. The multiplicity of infection (MOI) and the duration of the infection time will depend on the type of virus used and the cell line employed.

In a specific embodiment, described herein, 293 cells which had previously been transfected with a recombinant double-D expression vector, were infected with Ad5 at a MOI of 10. Forty-eight hours later the cells were frozen and thawed three times, and incubated for one hour at 56° C. to inactivate the adenovirus. The resulting cell lysate contains recombinant viral particles that may be used to infect cells or tissue of choice.

Alternatively, the recombinant double-D DNA vectors may be grown up and purified for use in DNA transfections, using any of the methods well known to those skilled in the art. (See Sambrook et al., 1989, Molecular Cloning: A Laboratory Manual, Cold Spring Harbor Laboratory Press, Cold Spring Harbor, N.Y., for description of methods that may be used to propagate recombinant vector DNA.)

5.4. USES OF RECOMBINANT VECTORS

The double-D expression vectors, containing a heterologous gene of interest and described herein, may be useful for therapeutic treatment of genetic disorders. The gene of interest may be the wild type complement of any mutated or defective gene and may be inserted into the double-D recombinant vectors so that its expression is controlled by its natural promoter (e.g., so that expression is regulated normally) or by a heterologous promoter.

The double-D expression vectors may be transfected into host cells using any of the techniques routinely used by the skilled artisan for efficient transfer of nucleic acids into host cells. Host cells may be transfected in vivo or in vitro. For example, cells may be removed from the host and transfected with recombinant vectors. The transfected cells may be assayed for proper integration of the recombinant DNA into chromosome 19 of the host. The cells may also be tested to determine whether the gene product of interest is properly expressed. Following the verification of proper integration and expression of the recombinant DNA, the transfected cells may be implanted or returned into the host.

Alternatively, transfer of recombinant DNA may take place in vivo. In a preferred embodiment of the invention the recombinant double-D vectors may be encapsulated into liposomes for delivery into host cells. Liposomes are spherical lipid bilayers with aqueous interiors. All molecules that are present in an aqueous solution at the time of liposome formation (in this case, recombinant vectors and/or REP protein) are incorporated into this aqueous interior. The liposomal contents are both protected from the external microenvironment and, because liposomes fuse with cell membranes, are efficiently delivered into the cell cytoplasm. The double-D vectors of the invention, may be co-encapsulated into liposomes with viral REP protein, RNA molecules encoding REP protein or viral DNA sequences encoding the REP protein, to provide for site specific integration of viral vector sequences into the host chromosome.

Additionally, recombinant viral stock may be generated by transfection of the double-D plasmid into a suitable host cell line that first allows for conversion of a circular duplex molecule into a linear DNA molecule covalently closed at both ends. This then permits replication and encapsidation of recombinant DNA into mature viral particles. The resulting viral stocks may then be used to infect tissue or cells affected by the genetic defect.

6. EXAMPLE: A NOVEL 165 BASE PAIR TERMINAL REPEAT IS THE ONLY cis-ELEMENT REQUIRED FOR ADENO-ASSOCIATED VIRUS LIFE CYCLE The subsection below describes the synthesis and functional characterization of the double-D sequence.

6.1. MATERIALS AND METHODS 6.1.1. DNA TRANSFECTION

Human cell line 293 was maintained in DMEM (Dulbecco modified Eagle medium, GIBCO) WITH 10% FCS (fetal calf serum, HyClone). Transfection of plasmid DNA was done by lipofection (BRL) method as described by the manufacturer. Briefly, cells in a 6-cm dish were washed twice with DMEM and infected with Adenovirus 5 at 10 moi (multiplicity of infection) in 1 ml Opti-MEM (GIBCO) for 1 hr. Then 5 ug plasmid DNA was incubated with 50 ul of lipofectin (BRL) at room temperature for 10 min, mixed with 2 ml of Opti-MEM and added to the Adenovirus infected cells. After incubation for 12 hrs., the cells were fed with 3 ml of DMEM containing 4% FCS and incubated for an additional 36 hours.

6.1.2. SOUTHERN HYBRIDIZATION

Low molecular weight DNA from transfected cells was extracted as described by Hirt (Hirt, B. 1967, J. Mol. Biol. 26:365–369). The DNA was digested by restriction enzymes (New England BioLab), separated on an agarose gel, then transferred onto the Genescreen plus Nylon membrane (DuPont). Hybridization with $^{32}$P labeled plasmid DNA was carried out as recommended by the manufacturer. Hybridization with r- $^{32}$P-ATP end-labeled ITR oligonucleotide probe A-1 (5'TTGGCCACTCCCTCTCTGCG3') (SEQ ID NO: 4), derived from A region of ITR, kindly provided by N. Muzyczka) was performed as follows: the membrane was prehybridized in 10 ml solution containing 5× SSC, 10× Denhardt's solution, 10% dextran sulfate and 5% SDS at 60° C. for at least 1 hr. 25 ng of $^{32}$P end labeled oligo-probe and 200 ug heat-denatured salmon sperm DNA in 0.5 ml H$_2$O were added. Hybridization was continued at 60° C. overnight. The membrane was washed twice in 3× SSC and 5% SDS at 60° C. for 30 minutes and once in 0.2× SSC at room temperature for 10 minutes. For Southern blot analysis of lacZ expressing cell clones a $^{32}$P labeled chromosome 19 specific probe was used (Samulski, R. J. et al., 1991, EMBO J. 10:3941–3950).

To determine whether the CMV/lacZ DNA fragments had integrated specifically into chromosome 19, high molecular weight genomic DNA was extracted from transfected cells as described by Sambrook et al. (1989, Molecular Cloning: A Laboratory Manual. Cold Spring Harbor Laboratory Press. Cold Spring Harbor, N.Y.). The genomic DNA was used as template in PCR reactions designed to amplify junction fragments. The following PCR primer was used in the PCR reaction.

5'-GTGAATTGTAATACGACTCACTATAGGGCG-3' (SEQ ID NO: 7).

6.1.3. PCR AND CONSTRUCTION OF ITR PLASMID

Low molecular weight DNA from AAV and Ad5 infected cells was used as template for the PCR reaction with a single primer derived from D-sequence of AAV. The PCR was performed at 94° C. 1 min., 45° C. 30 seconds and 72° C. 1 min. for 35 cycles in a 50 ul reaction solution containing 20 mM Tris-HCl (pH8.8), 1.5 mM MgCl, 50 mM KCl, 2.5% formamide, 100 uM dATP, dCTP and dTTP, 75 uM 7-deazo-dGTP, 25 uM dGTP, 1.5 U AmpliTaq (Perkin Elmer Cetus), 1 ng AAV DNA and 100 pmole primer TR-1 (5'-GGAATTCAGGAACCCCTAGTGATGG3-3') (SEQ ID NO: 3). The PCR product was purified by agarose gel electrophoresis, cut with EcoRI and ligated with an EcoRI cut and dephosphorylated pGEM 3Z plasmid (Promega). The ligated plasmid was transformed into *E.coli* Sure strain (Stratagene). Positive clones named pDD's were screened for the presence of double-D terminal repeat and confirmed by dideoxy-sequencing with 7-deazo-dGTP substituted for dGTP (Sanger, F. et al., 1977, Proc. Natl. Acad. Sci. USA 74:5463–5467). Subsequently, a neo gene was cloned into the SalI site of pDD-2 resulting in the plasmid pDD-neo.

6.1.4. CLONING OF NEO-RESISTANT CELL LINES

Ad5 infected 293 cells were cotransfected with pDD-neo and pAAV/Ad (Samulski, et.al., 1989. J. Virol. 63:3822–3828) for 48 hrs. The cells were frozen and thawed three times and then incubated at 56° C. for 1 hour to inactivate the Ad5 virus. The cell lysate containing the DD-neo recombinant AAV virus was used to infect the human cell line Detroit 6. The cells were inoculated for 24 hours, then selected with G418 at 400 ug/ml to obtain neo-resistant clones. Various clones were superinfected with wild-type AAV and Ad5 at a MOI of 10 to rescue the latent neo-AAV.

6.2. RESULTS

6.2.1. CONSTRUCTION OF ITR WITH DOUBLE D SEQUENCE

The Polymerase Chain Reaction (PCR) was used to construct the inverted terminal repeat with a D' sequence added to the other end. The rationale is based on the T-shape structure of the ITR. In the first round of PCR reaction, the AAV viral IRT will self-prime the elongation to produce a long T-shaped hairpin structure containing D and D' on the stem. Upon denaturation, this DNA can serve as template for single-primed PCR.

Because of the high GC content and the strong palindromic structure in the ITR region, several strategies such as 7-deazo-dGTP, 2.5% formamide, and high concentration of primer were utilized to tackle the PCR problems and yield sufficient desired PCR product. For the convenience of cloning, an EcoRI recognition sequence was attached to the 5' of the primer so that the PCR product can be cut by EcoRI and easily cloned into the polylinker of pGEM 3Z. Due to the instability of the ITR in bacteria host, the recombinant plasmid was transformed into an *E.coli* SURE strain (Stratagene) in which the ITR was rather stable. By using the above strategy, we obtained numerous positive clones. Some clones were characterized by restriction digestion and sequencing. One of the clones is shown in FIG. 2 bearing an insert of D'ABB'CC'A'D in the EcoRI site of the pGEM-3Z. This plasmid was named pDD-2 and was used in the following transfection experiments.

6.2.2. pDD-2 REPLICATION IS DEPENDENT ON REP

In order to assay the capability for replication, Plasmid pDD-2 was transfected into Ad5 infected 293 cells with or without cotransfection of a helper plasmid pAAV/Ad, which contains functional REP and CAP genes but without the ITR, so that it can not replicate. Due to the lack of functional origins this molecule can only supply REP and CAP proteins in trans. Post transfection for 48 hours, the plasmid DNA was extracted and separated on 1% agarose gel with or without DpnI digestion. DpnI only digests the input methylated plasmid DNA while leaving the replicated (demethylated) DNA intact. The results demonstrated that in the absence of the helper plasmid, pDD-2 plasmid did not replicate therefore the DNA is completely DpnI sensitive (FIG. 3, lane 1 and 2). However, in the presence of the helper plasmid, pDD-2 replicated very efficiently as evidenced by the resistance to DpnI digestion and the existence of monomer and dimer molecules: the typical AAV replication pattern (FIG. 3, lane 3 and 4). The pDD-2 replication is dependent on two factors: the double-D in cis and REP gene products in trans, because the cloning vector pGEM-3Z did not replicate under the same conditions and a plasmid containing only REP gene without CAP gene can also supply the helper function in trans for pDD-2 (data not shown).

Since the replication of pDD-2 with one modified ITR was very efficient, a comparison was made between pDD-2 and two other infectious AAV plasmids, psub201 [Samulski, et.al., 1987. J. Virol, 61:3096–3101.] and pSM620 [Samulski, et.al., 1982, Proc. Natl. Acad. Sci. U.S.A. 79:2077–2081.], which possesses two ITRs as well as wild type REP and CAP genes. The pDD-2 was cotransfected into Ad5 infected cells with equal amounts of either pAAV/Ad helper (without ITR), psub201 or pSM620. The plasmid DNA was extracted 2 days post transfection, digested with DpnI, separated on 1% agarose gel. Southern blot was performed with an oligonucleotide probe from the A sequence of the ITR so that it can detect all the replicated DNA containing ITRs. As shown in FIG. 4, all three plasmids containing AAV coding genes can complement the pDD-2 replication equally well. However, psub201 itself replicated at a much lower level although it can complement pDD-2 replication effectively. pSM201 replicated at a similar level as pDD-2.

In order to determine whether the effectiveness of pDD-2 replication was due to the special double-D or due to the smaller size of the plasmid (2.9 kb), a neo gene fragment of 1.2 kb was inserted into the SalI site at the polylinker of pDD-2. The new plasmid pDD-neo is 4.1 kb in size, close to the size of wild type AAV (4.68 kb). This plasmid converted from a duplex circular to a linear molecule and replicated as efficiently as the parental pDD-2 (FIG. 5). double-D plasmids were constructed with sizes up to 7.5 kb . These molecules also efficiently replicate (data not shown). The above results suggest that the double-D is an excellent substrate for Rep-dependent replication.

6.2.3. REPLICATION AND RESCUE IS VIA AAV MECHANISM

AAV inverted terminal repeats have been proven to be the viral replication origins. In vitro, these sequences are recognized as a substrate by REP protein, a site-and-strand-specific nickase and helicase. ITRs have also been considered as the substrate for AAV rescue [Muzyczka, N. 1992, Current Topics in Microbiology & Immunology. 158, 97–129]. Since the double-D plasmids contain one unique ITR and we have demonstrated that this sequence replicates only in the presence of REP proteins, it is attractive to predict that the rescue and replication are through similar AAV rescue and replication mechanisms (FIGS. 1, A and B).

In order to test the above assumption, pDD-2 DNA was transfected into Ad5 infected 293 cells with or without helper plasmid, or transfected into uninfected 293 cells. Subsequently, the plasmid DNA was subjected to restriction analysis by two single cutter enzymes ScpI and ScaI respectively (for map, see FIG. 2). The DNA was probed with ITR oligonucleotide so that only the ITR-containing fragments would be detected. The results are shown in FIG. 6. After SspI or ScaI digestion, a linear full length plasmid band could be observed throughout all the lanes (P to 6). This band was derived from the unresolved input circular plasmid. While in lane 1 and 4 (Ad5 plus helper plasmid), four additional bands with expected molecular weight could also be seen. Two of them arose from internal head-to-head and tail-to-tail fragments of the digested dimer molecules. The other two bands are derived by digested monomer and dimer external fragments, most likely suggesting that pDD-2 is resolved at the unique double-D site and replicated via AAV replication scheme. It is noteworthy that in Ad5 infected cells (lane 2 and 5) and uninfected cells (lane 3 and 6), two fainter bands from the resolved monomer were also visible, suggesting that some cellular mechanism can initiate the rescue process at the double-D site in the absence of any other AAV sequence or AAV gene product. Although, such rescued DNA could not replicate in the absence of Rep proteins (see FIG. 3, lane 2) this suggests that the double D substrate may confer special features involved in the first step of AAV recognition not seen with the conventional AAV plasmids containing two wild type ITR's.

6.2.4. ONE DOUBLE-D IN-CIS IS SUFFICIENT FOR AAV VIABILITY

Plasmid pDD-neo was used to generate the DD-neo virus preparation as described in Section 6.1.4. The cell lysates containing the recombinant virus particles were then used to infect human Detroit 6 cells. Two weeks post infection cells were selected against G418. A number of neo-resistant clones were isolated, indicating that the recombinant viruses were made and transduction was accomplished. DD-neo resistant cell lines were superinfected with wild type and AAV-2 and Ad5 and assayed for transduced DNA rescue and replication. Then the viral DNA was extracted and probed with a neo gene fragment. Examples of DD-neo$^r$ cell lines that rescued DD-neo viral DNA replicated as monomer and dimer (data not shown). These results demonstrated that the 165 bp single double-D is the only cis-sequence required to fulfill all the steps in AAV life cycle. Thus, the processes such as rescue from the plasmid, replication of the DNA, encapsidation of the virus, infection into the cells, integration into the chromosome and rescue back again were all mediated by this unique double D inverted terminal repeat sequence.

6.2.5. TRANSFECTION OF DOUBLE-D RECOMBINANT VECTORS

Human 293 cells were transfected with either double-D ITR CMV/LacZ constructs or CMV/LacZ constructs lacking the double-D sequences. These particular constructs contain the lacZ gene which encodes the *E. coli* β-galactosidase reporter protein, under the transcriptional control of the CMV (cytomegalovirus) constitutive promoter. In addition, the CMV/LacZ plasmids were cotransfected with pHIV-REP, a recombinant plasmid containing the gene encoding AAV REP protein under the transcriptional control of the HIV promoter (Antoni, B. A. et al., 1991, J. Virology 65:396–404).

Six weeks post-transfection cells were stained to determine what percent of the cells were expressing β-galactosidase activity. Detection of β-galactosidase activity in cell extracts indicates the presence of chromosomally integrated lacZ constructs. only the double-D CMV/LacZ constructs that were cotransfected with a vector capable of expressing the REP protein were found to be expressing β-galactosidase activity.

Southern Blot analysis of the transfected cells confirmed that those cells expressing β-galactosidase activity had integrated the double-D CMV/LacZ constructs into their genome (FIGS. 11 and 12). In addition, PCR analysis indicated that the CMV/LacZ plasmids had integrated into the specific region of chromosome 19 into which wild type AAV normally integrates (TABLE I) (SEQ ID NO: 8–13).

TABLE I

Cells: TA55, TA67, TA69:

GTGAATTGTAATACGACTCACTATAGGGCGAATTCAGGAACCCCTAGTGATGGAGT
TGGCCACTCCCTCACTGCGCGCTCGCTCGCTCACTGAGGCCG<u>ACGGTATCAGCGCC</u>
<u>CTGCACCAGGTCAGCGCCCCCCGC</u>
AAV sequence is joined to BamHI fragment of chromosome 19 at position 1695.
Cells: TA8, TA22, TA65, TA76:

GTGAATTGTAATACGACTCACTATAGGGCGAATTCAGGAACCCCTAGTGATGGAGT
TGGCCACTCCCTCACTGCGCGCTCGCTCGCTCACCGCAGCG<u>AGGCCTGGGCTTTGC</u>
<u>CACCCTATGGT</u>
AAV sequence is joined to BamHI fragment of chromosome 19 at position 1830.
Cells: TA18. TA29:

GTGAATTGTAATACGACTCACTATAGGGCGATTCAGGAACCCCTAGTGATGGAGTT
GGCCACTCCCTCACTGCGCGCTCGCTCGCTCACTGAXGG<u>CTTTGCCACCCTATGGT</u>
<u>GACACCCC</u>
AAV sequence is joined to BamHI fragment of chromosome 19 position 1836.
Cell: TA60, TA68:

GTGAATTGTAATACGACTCACTATAGGGCGATTCAGGAACCCCTAGTGATGGAGTT
GGCC<u>ACCCTATGCTGACACCCCGTCCC</u>
AAV sequence is joined to BamHI fragment of chromosome 19 at position 1843.
Cells: TA16:

GTGAATTGTAATACGACTCACTATAGGGCGAATTCAGGAACCCCTAGTGATGGAGTT
GGCCACTCCCTCACTGCGCGCTCGCTCGCTCA<u>CCCCCACTTCCGAATTGGAGCCGC</u>
AAV sequence is joined to BamH-I fragment of chromosome 19 at position 1891.
Cells: TA45, TA63, TA64, TA70, TA75, TA88:

GTGAATTGTAATACGACTCACTATAGGGCGAATTCAGGAACCCCTAGTGATGGAGT
TGGCCACTCCCTCACTGCGCGCTCGCTCGCTCACTGAGGCCGGGCGACCAAAGGTT

TABLE I-continued

CGCCGACGCCCGGGCTTTGCCC<u>TCTCCTGAACCTGAG</u>
AAV sequence is joined to chromosome 19 at position 2143.

Sequences of Chromosome 19 are underlined.

These data indicate the following: (i) that only cis-acting sequence required for targeted integration by AAV is the double-D sequence and (ii) the AAV REP protein is sufficient to act in trans to target site specific integration of recombinant vector DNA into genomic host DNA.

The present invention is not to be limited in scope by the exemplified embodiments disclosed herein which are intended as illustrations of single aspects of the invention, and any clones, DNA or amino acid sequences which are functionally equivalent are within the scope of the invention.

Indeed, various modifications of the invention, in addition to those shown and described herein, will become apparent to those skilled in the art from the foregoing description and accompanying drawings. Such modifications are intended to fall within the scope of the appended claims.

It is also to be understood that all base pair and amino acid residue numbers and sizes given for nucleotides and peptides are approximate and used for the purposes of description. Various publications are cited herein that are hereby incorporated by reference in their entireties.

What is claimed is:

1. A purified and isolated nucleic acid molecule having a single adeno-associated virus inverted terminal repeat sequence and an additional 20 basepair D sequence (SEQ ID NO: 5), wherein said nucleic acid molecule:
   (a) hybridizes under highly or moderately stringent hybridization conditions to the sequence depicted in FIG. 9 (SEQ ID NO: 1); and
   (b) which directs the replication and assembly into adeno-associated virus particles and/or integration into the host genome, of recombinant DNA containing said nucleic acid molecule.

2. A purified and isolated nucleic acid molecule having a single adeno-associated virus inverted terminal repeat sequence and an additional 20 basepair D sequence (SEQ ID NO: 5), wherein:
   (a) the 20 basepair D sequence hybridizes under highly or moderately stringent hybridization conditions to the sequence depicted in FIG. 9 (SEQ ID NO: 1); and
   (b) which nucleic acid molecule directs the replication and assembly into adeno-associated virus particles and/ or integration into the host genome, of recombinant DNA containing said nucleic acid molecule.

3. A recombinant DNA vector comprising a DNA nucleotide sequence encoding a protein of interest and the nucleic acid molecule of claim 1 or 2.

4. A method of replicating and encapsidating a recombinant DNA molecule into an adeno-associated virus particle, comprising:
   a) culturing a eukaryotic cell containing (i) a helper virus which replicates in said eukaryotic cells, (ii) a recombinant nucleic acid encoding adeno-associated virus REP and CAP proteins, and (iii) a recombinant nucleic acid that contains a DNA sequence of interest and the nucleic acid molecule of claim 1 or 2; whereby the recombinant nucleic acid containing the DNA sequence of interest and the nucleic acid molecule of claim 1 or 2 is replicated and assembled into adeno-associated virus particles; and
   b) collecting adeno-associated virus particles.

5. A method of transferring a nucleic acid molecule into an isolated eukaryotic cell comprising transfection of said eukaryotic cell with a recombinant DNA molecule containing the nucleic acid molecule of claim 1 or 2.

6. A method of transferring a nucleic acid molecule into an isolated host cell comprising:
   (a) encapsulating a recombinant DNA molecule containing the nucleic acid molecule of claim 1 or 2 or a 165 base pair inverted terminal repeat sequence as depicted in FIG. 9 (SEQ ID NO: 1) into a liposome; and
   (b) administering the liposome preparation to said isolated host cell.

7. A stock of recombinant adeno-associated virus comprising a packaged recombinant DNA molecule containing the nucleic acid molecule of claim 1 or 2 a 165 base pair inverted terminal repeat sequence as depicted in FIG. 9 (SEQ ID NO: 1).

8. An isolated eukaryotic cell comprising a recombinant DNA molecule containing the nucleic acid molecule of claim 1 or 2.

9. The recombinant DNA vector according to claim 3 further comprising a DNA nucleotide sequence that encodes the adeno-associated virus REP and CAP proteins.

10. The recombinant DNA vector according to claim 3 further comprising a DNA nucleotide sequence recognized by bacterial gamma delta resolvase as depicted in FIG. 10 (SEQ ID NO: 2).

11. The method of claim 6 in which a nucleic acid molecule encoding the adeno-associated virus REP protein is co-encapsulated with the recombinant DNA molecule.

12. The method of claim 6 in which AAV REP protein is co-encapsulated with the recombinant DNA.

13. The recombinant DNA vector according to claim 9 further comprising a DNA nucleotide sequence recognized by bacterial gamma delta resolvase as depicted in FIG. 10 (SEQ ID NO: 2).

14. A method of replicating and encapsidating a recombinant DNA molecule into an adeno-associated virus particle, comprising:
   a) culturing a eukaryotic cell containing (i) a helper virus which replicates in said eukaryotic cells, (ii) a recombinant nucleic acid encoding adeno-associated virus REP and CAP proteins, and (iii) a recombinant nucleic acid that contains a DNA sequence of interest and a 165 base pair inverted terminal repeat sequence as depicted in FIG. 9 (SEQ ID NO: 1); whereby the nucleic acid containing the 165 base pair inverted terminal repeat sequence and the DNA sequence of interest is replicated and assembled into adeno-associated virus particles; and
   b) collecting adeno-associated virus particles.

15. The method according to claim 14 in which the recombinant nucleic acid containing the DNA sequence of interest and the 165 base pair terminal repeat sequence is a plasmid vector comprising:
   (a) a promoter;
   (b) a DNA sequence of interest transcribed under the control of the promoter; and
   (c) a 165 base pair inverted terminal repeat sequence as depicted in FIG. 9 (SEQ ID NO: 1).

16. The method according to claim 14 in which the recombinant nucleic acid containing the DNA sequence of interest and the 165 base pair terminal repeat sequence is a plasmid vector comprising:
   (a) a promoter;

(b) a DNA sequence of interest transcribed under the control of the promoter; and (c) the nucleic acid molecule of claim 1 or 2.

17. The method according to claim 14 or 4 in which the helper virus is an adenovirus.

18. The method according to claim 14 or 4 in which the helper virus is a herpes simplex virus.

19. The method according to claim 14 or 4 in which the recombinant nucleic acid encoding the adeno-associated virus REP and CAP proteins is a plasmid vector comprising:

(a) promotors which control the expression of the adeno-associated virus REP and CAP RNA;

(b) translation initiation signals for the REP and CAP mRNA;

(c) DNA sequences encoding the REP and CAP proteins; and (d) transcriptional termination signals.

20. A method of replicating and encapsidating a recombinant DNA molecule into an adeno-associated virus particle, comprising:

(a) treating a recombinant nucleic acid comprising a 165 base pair terminal repeat sequence as depicted in FIG. 9 (SEQ ID NO: 1) and at least two bacterial gamma delta resolvase recognition sequences as depicted in FIG. 10 (SEQ ID NO: 2), with bacterial gamma delta resolvase enzyme; and (b) culturing a eukaryotic cell containing a helper virus and said resolvase treated recombinant nucleic acid; whereby the resolved recombinant nucleic acid is replicated and encapsidated into a viral particle.

21. The method according to claim 20 in which the helper virus is an adenovirus.

22. The method according to claim 20 in which the helper virus is a herpes simplex virus.

23. The method according to claim 20 in which the recombinant nucleic acid containing the bacterial gamma delta resolvase recognition sequences is a plasmid vector comprising:

(a) at least two bacterial gamma delta resolvase recognition sequences;

(b) a promoter;

(c) a DNA sequence of interest transcribed under the control of a promoter; and (d) a 165 base pair inverted terminal repeat sequence as depicted in FIG. 9 (SEQ ID NO: 1).

24. The method according to claim 20 in which the recombinant nucleic acid containing the bacterial gamma delta resolvase recognition sequences is a plasmid vector comprising:

(a) at least two bacterial gamma delta resolvase recognition sequences;

(b) a promoter;

(c) a DNA sequence of interest transcribed under the control of a promoter;

(d) a 165 base pair inverted terminal repeat sequence as depicted in FIG. 9 (SEQ ID NO: 1); and (e) a DNA nucleotide sequence that encodes the adeno-associated virus REP and CAP proteins.

25. An isolated host cell which replicates a helper virus and which produces stocks of recombinant adeno-associated viruses, said cell comprising (i) a helper virus, (ii) a recombinant nucleic acid encoding adeno-associated virus CAP and REP proteins, and (iii) a recombinant nucleic acid that contains a DNA sequence of interest and a 165 base pair inverted terminal repeat sequence as depicted in FIG. 9 (SEQ ID NO: 1);

whereby the nucleic acid containing the 165 base pair inverted terminal repeat sequence and the DNA sequence of interest is replicated and assembled into adeno-associated virus particles.

\* \* \* \* \*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 165 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:1:

```
AGGAACCCCT  AGTGATGGAG  TTGGCCACTC  CCTCTCTGCG  CGCTCGCTCG  CTCACTGAGG      60

CCGGGCGACC  AAAGGTCGCC  CGACGCCCGG  GCTTTGCCCG  GGCGGCCTCA  GTGAGCGAGC     120

GAGCGCGCAG  AGAGGGAGTG  GCCAACTCCA  TCACTAGGGG  TTCCT                     165
```

( 2 ) INFORMATION FOR SEQ ID NO:2:

( i ) SEQUENCE CHARACTERISTICS:
        ( A ) LENGTH: 120 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:2:

```
CCCTGTATCC  TAAATCAAAT  ATCGGACAAG  CAGTGTCTGT  TATAACAAAA  AATCGATTTA      60

ATAGACACAC  CAACAGCATG  GTTTTTATGT  GTGCGATAAT  TTATAATATT  TCGGACAGGG     120
```

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:3:

```
GGAATTCAGG  AACCCCTAGT  GATGG                                               25
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:4:

```
TTGGCCACTC CCTCTCTGCG                                                      20
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:5:

```
AGGAACCCCT AGTGATGGAG                                                      20
```

( 2 ) INFORMATION FOR SEQ ID NO:6:

( i ) SEQUENCE CHARACTERISTICS:
        ( A ) LENGTH: 145 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:6:

```
AGGAACCCCT CGTGCTGGCG TTGGCCACTC CCTCTCTGCG CGCTCGCTCG CTCACTGAGG          60
CCGCCCGGGC AAAGCCCGGG CGTCGGGCGA CCTTTGGTCG CCCGGCCTCA GTGAGCGAGC         120
GAGCGCGCAG CGCGGGCGTG GCCAA                                              145
```

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

```
 GTGAATTGTA ATACGACTCA CTATAGGGCG                                          30
```

( 2 ) INFORMATION FOR SEQ ID NO:8:

( i ) SEQUENCE CHARACTERISTICS:
        ( A ) LENGTH: 139 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

```
 GTGAATTGTA ATACGACTCA CTATAGGGCG AATTCAGGAA CCCCTAGTGA TGGAGTTGGC         60
```

CACTCCCTCA CTGCGCGCTC GCTCGCTCAC TGAGGCCGAC GGTATCAGCG CCCTGCAGCA  120

CCAGGTCAGC GCCCCCCGC  139

( 2 ) INFORMATION FOR SEQ ID NO:9:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GTGAATTGTA ATACGACTCA CTATAGGGCG AATTCAGGAA CCCCTAGTGA TGGAGTTGGC  60

CACTCCCTCA CTGCGCGCTC GCTCGCTCAC CGCAGCGAGG CCTGGGCTTT GCCACCCTAT  120

GGT  123

( 2 ) INFORMATION FOR SEQ ID NO:10:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GTGAATTGTA ATACGACTCA CTATAGGGCG ATTCAGGAAC CCCTAGTGAT GGAGTTGGCC  60

ACTCCCTCAC TGCGCGCTCG CTCGCTCACT GANGGCTTTG CCACCCTATG GTGACACCCC  120

( 2 ) INFORMATION FOR SEQ ID NO:11:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GTGAATTGTA ATACGACTCA CTATAGGGCG ATTCACCCTA GTGATGGAGT TGGCCACCCT  60

ATGCTGACAC CCCGTCCC  78

( 2 ) INFORMATION FOR SEQ ID NO:12:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GTGAATTGTA ATACGACTCA CTATAGGGCG AATTCAGGAA CCCCTAGTGA TGGAGTTGGC  60

CACTCCCTCA CTGCGCGCTC GCTCGCTCAC CCCCACTTCC GAATTGGAGC CGC  113

( 2 ) INFORMATION FOR SEQ ID NO:13:

( i ) SEQUENCE CHARACTERISTICS:
        ( A ) LENGTH: 149 base pairs
        ( B ) TYPE: nucleic acid -continued ( C ) STRANDEDNESS: single
( D ) TOPOLOGY: linear ( i i ) MOLECULE TYPE: DNA ( x i ) SEQUENCE DESCRIPTION: SEQ ID NO:13:

```
GTGAATTGTA  ATACGACTCA  CTATAGGGCG  AATTCAGGAA  CCCCTAGTGA  TGGAGTTGGC      60

CACTCCCTCA  CTGCGCGCTC  GCTCGCTCAC  TGAGGCCGGG  CGACCAAAGG  TTCGCCGACG     120

CCCGGGCTTT  GCCCTCTCCT  GAACCTGAG                                          149
```